(12) United States Patent
Jones et al.

(10) Patent No.: US 7,785,584 B2
(45) Date of Patent: *Aug. 31, 2010

(54) OINTMENT WOUND SPRAY

(75) Inventors: David P. Jones, San Antonio, TX (US); Robert Espinoza, San Benito, TX (US)

(73) Assignee: Healthpoint, Ltd., San Antonio, TX (US)

(*) Notice: Subject to any disclaimer, the term of this patent is extended or adjusted under 35 U.S.C. 154(b) by 1078 days.

This patent is subject to a terminal disclaimer.

(21) Appl. No.: 10/639,991

(22) Filed: Aug. 13, 2003

(65) Prior Publication Data

US 2005/0036950 A1    Feb. 17, 2005

(51) Int. Cl.
*A61K 38/46* (2006.01)
*A61K 38/48* (2006.01)

(52) U.S. Cl. .......... 424/94.65; 424/94.64; 424/94.66; 424/94.1; 424/94.2

(58) Field of Classification Search ........... 424/400, 424/401, 43, 45, 78.02, 78.03, 78.05, 78.06, 424/94.1, 94.64, 94.65, 94.66, 94.67; 514/829, 514/830, 932
See application file for complete search history.

(56) References Cited

U.S. PATENT DOCUMENTS

| | | | |
|---|---|---|---|
| 2,917,433 A | 12/1959 | Goldman | |
| 3,983,209 A | 9/1976 | Schmitt | 424/78 |
| 4,366,169 A | 12/1982 | White | |
| 4,372,785 A | 2/1983 | Lawson et al. | 106/162.9 |
| 5,152,983 A | 10/1992 | Nambudiry et al. | 424/60 |
| 5,284,833 A | 2/1994 | McAnalley et al. | |
| 5,536,502 A | 7/1996 | Mulder | |
| 5,543,149 A * | 8/1996 | Rubin | 424/405 |
| 5,565,189 A | 10/1996 | Mulder | |
| 5,589,156 A | 12/1996 | Henry | |
| 5,631,019 A | 5/1997 | Marx | |
| 5,874,479 A | 2/1999 | Martin | |
| 5,879,688 A * | 3/1999 | Coury et al. | 424/401 |
| 5,922,349 A * | 7/1999 | Elliesen et al. | 424/449 |
| 5,981,606 A | 11/1999 | Martin | |
| 6,046,178 A * | 4/2000 | Silvetti, Sr. | 514/60 |
| 6,093,411 A * | 7/2000 | Bissett | 424/401 |
| 6,117,915 A | 9/2000 | Pereira et al. | |
| 6,395,269 B1 | 5/2002 | Fuller et al. | 424/89 |
| 6,416,769 B1 * | 7/2002 | Vromen | 424/401 |
| 6,458,551 B1 | 10/2002 | Wilkinson | |
| 6,479,060 B1 | 11/2002 | Jones et al. | |
| 6,548,556 B2 | 4/2003 | Hobson et al. | |
| 6,875,425 B2 | 4/2005 | Harichian et al. | 424/59 |
| 2002/0045600 A1* | 4/2002 | Schwarzman | 514/100 |
| 2002/0114798 A1 | 8/2002 | Hobson et al. | 424/94.63 |

FOREIGN PATENT DOCUMENTS

| | | |
|---|---|---|
| DE | 101 00 015 | 8/2002 |
| DE | 101 00 015 A1 | 8/2002 |
| EP | 0194647 | 9/1986 |
| EP | 0 498 532 A1 | 8/1992 |
| EP | 0498532 | 8/1992 |
| EP | 0576279 | 12/1993 |
| EP | 0674001 | 9/1995 |
| EP | 1 247 519 | 4/2001 |
| JP | 3294211 | * 12/1991 |
| WO | WO 95/23614 | 9/1995 |
| WO | WO 98/55604 | 12/1998 |
| WO | WO 02/051436 | 7/2002 |

OTHER PUBLICATIONS

CRODAFOS (Feb. 12, 2002).*
Yoshii S. et al., "Prevention of surgical site infection by antibiotic spraying in the operative field during cardiac surgery", Jpn J Thorac Cardiovasc Surg May 2001; 49(5):279.81 Abstract.
Soroff HS et al., "Collagenase ointment and polymyxin B sulfate/bacitracin spray versus silver sulfadiazine cream in partial-thickness burns: a pilot study", J Burn Care Rehabil Jan.-Feb. 1994; 15(1):13-7 Abstract.
Wright VC et al, "Use of a topical triple-antibiotic spray to reduce morbidity from pelvic infection after gynecologic operations", Can J Surg Jul. 1980; 23(4):366-9, 372 Abstract.
CRODAFOS CS-20 Acid, INCI Name: Cetearyl Alcohol (and) Dicetyl Phosphate, Article from Personal Care, CRODAFOS CS-20 Acid, DS-156R-2, Feb. 12, 2002, pp. 1-11.
"Sprayable emulsion solution from Croda," Press Release, www.croda.co.uk, Jun. 2002.
Wilhardt, Michaelle et al. "National PBM Drug Monograph Papain-Urea (Accuzyme®) and Papain-Urea-Chlorophyllin Copper Complex Sodium (Panafil®)" Jan. 2004 XP-002302635 pp. 1-10; www.vapbrn.org.

* cited by examiner

*Primary Examiner*—Marianne Seidel
(74) *Attorney, Agent, or Firm*—Fulbright & Jaworski L.L.P.

(57) ABSTRACT

A spray-on topical wound debrider spray is prepared forming a mist, spray or foam which will not drip significantly after application. The preferred wound debrider is papain. The spray contains a surfactant emulsifier admixture having a composition viscosity of from about 5000 cps to about 50,000 cps and is preferably a fatty alcohol phosphate ester emulsifier composition.

34 Claims, No Drawings

OINTMENT WOUND SPRAY

FIELD OF THE INVENTION

The invention relates to topical spray-on pharmaceutical compositions that contain as topically active agents, proteolytic wound debriders.

BACKGROUND OF THE INVENTION

Topical wound treatment pharmaceutical compositions are, of course, well known. They can include wound debriders, wound cleaners, wound healing agents, anti-microbials, anti-fungals, skin conditioning agents, etc. Regardless of the specific use, common to pharmaceutically satisfactory topical actives is the fact they all have in common that they must stay on the skin surface for a sufficient period of time to allow the active to perform; they must not irritate the skin; and, they must be perceived by the patient as pharmaceutically elegant or the patient will simply not use them. Pharmaceutically elegant, as those skilled in the art know, means the feel to the patient is good.

For topicals used in hospitals, they must be easy to apply by nurses and technicians, especially for ulcerated wounds they must not tear skin, and the feel must not be too greasy.

For many topicals, especially those used to apply to skin wounds, the most satisfactory administration format is a spray-on. Advantages of a spray-on are many. First, the applying nurse or technician does not have to touch the wound. Secondly, avoiding wound contact avoids contamination. Third, further wound disturbance is avoided. For these reasons, the spray-on technique is highly preferred.

The use of a spray-on technique with many topicals is however problematic for several reasons. Amongst those reasons is the fact that normally a spray-on liquid is thin and can drip from the wound site especially if the wound is on an extremity and in a vertical position. Also, where aerosols are employed, as opposed to simply air pump systems, the aerosol mist is not easily directed to the wound which can then cause considerable overspray. In this respect, spray-on administration has at least one disadvantage over ointment dispensed from a tube that can be placed directly into the wound. Placement is not a problem. There is therefore a need existing for a product line of topically-active wound treatment compositions that can be sprayed and precisely directly onto the wound and that will stay in place in the wound bed, without dripping out and that will uniformly distribute a wound debrider.

Accordingly, it is a primary objective of this invention to provide a topical pharmaceutical composition for use on skin wounds by topically spraying on the wound site with the composition having the characteristic that it can be spray directed accurately, is thin enough to create a mist or foam, and yet will not drip from the wound site even if the wound, for example, on an extremity is in a vertical position.

The method of accomplishing this and other objectives of the invention will become apparent from the detailed description of the invention which follows hereinafter.

SUMMARY OF THE INVENTION

A spray-on topical wound debrider composition, preferably a wound debrider spray or foam, is prepared which will not drip significantly after application. The preferred wound debrider is papain. The composition contains a surfactant emulsifier admixture forming an emulsion having a total composition viscosity of from about 5000 cps to about 50,000 cps. The emulsifier is preferably a fatty alcohol phosphate ester emulsifier composition. This combination effectively carries and uniformly distributes the proteolytic enzyme which is an important feature of the invention.

DETAILED DESCRIPTION OF A PREFERRED EMBODIMENT

For describing the compositions certain definitional terms are appropriate. "Pharmaceutically elegant" has been previously defined. The "pharmaceutical composition" and/or "the composition" as used throughout the present specification and the accompanying claims is to be understood as defining compositions of which the individual components or ingredients are themselves pharmaceutically acceptable, e.g. that is they are topically acceptable. Put another way, they are non-irritants, and they are either FDA approved or on the GRAS safe list. The term "topically active ingredient" and/or "topically active pharmaceutical" is intended to be non-limiting and includes those pharmaceutical active agents that are commonly applied topically such as waterproofing agents, skin barrier/skin protectant agents, skin conditioning agents, solvents, bio-adhesives, acne actives, analgesics, anesthetics, anorectals, antihistamines, anti-inflammatory agents, antibiotics, antifungals, antivirals, antimicrobials, scabicides, pediculicides, antineoplastics, antiperspirants, antipruritics, antisporadics, antiseborrheics, biologically active proteins and peptides, burn actives, cauterizing agents, depigment agents, diaper rash agents, enzymes, hair grow actives, kerotolytics, canker sore actives, cold sore actives, dental actives, saliva actives, photosensitizing actives, steroids, sunburn actives, sunscreens, wart actives, wound dressings of all types and retinol, retinoic acid and retinoic acid derivatives, etc. It is understood that this list is by way of example and not a limitation with respect to the active.

For the present invention, the most preferred topically active ingredients, and the ones for which the composition is specifically designed, are those that are used directly on skin wounds, which are wound debriders, wound cleaners, wound healing agents, anti-microbials, and antifungals. The most preferred are wound debriders.

For the topically active ingredients mentioned herein, the amounts used will very widely depending upon the topically active ingredient employed but generally will range from about 0.001% by weight to about 20% by weight of the composition and more typically from about 0.01% by weight to 10% by weight of the composition. The topically active ingredient that is the most preferred are wound debriders; and it is preferred that the debriding agent be a proteolytic enzyme used in amounts within the above described ranges.

As those skilled in the art know, a proteolytic enzyme will have in part or in total the capacity to hydrolyze peptide amide bonds. Such enzymes may also have some inherent lipolytic and/or amylolitic activity associated with the proteolytic activity. The preferred proteolytic enzyme is papain. Other suitable proteolytic enzymes include trypsin, chymo-trypsin, streptokinaise, streptodormase, ficin, pepsin, carboxypeptidase, aminopeptidase, chymopapain, bromelin, thermolysin, thermoase, collagenase, and other proteolytic enzymes.

Papain is a proteolytic enzyme derived from the native green fruit of the tropical papaw or melon tree (*Carica papaya*) whose clear watery fluid is collected, dried, powdered, and sieved to produce the papain. It is white to gray powder and is moderately hygroscopic. Papain has wide specificity. It will degrade most protein substrates more extensively than the pancreatic proteases. It is also an esterase. Papain is very soluble in water and glycerine, but almost insoluble in alcohol. High Active Purified Papain, commercially available from Enzybel (Belgium), is a highly refined papain with a potency of about 50,000 USP units/mg. This material is supplied as a white to tan colored powder with low odor. Purified Papain Concentrate, commercially available from Enzyme Development Corporation, is a refined papain with a potency of about 35,000 USP units/mg.

Besides cysteine proteases, other groups of suitable proteolytic enzymes include those which are substantially free of sulfhydryl groups or disulfide bonds, and include the serine proteases, aspartic proteases and metallo-peptidases, particularly those derived from *Bacillus* and *Streptomiasis* bacteria and aspergilis molds.

Within this latter grouping, the more preferred enzymes are the *Bacillus* derived alkaline proteases generally called subtilisin enzymes. Reference is made to Deayl, L., Moser, P. W. and Wildi, B. S., "Proteases of the Genus *Bacillus*, II alkaline Proteases." Biotechnology and Bioengineering, Vol XII, pp. 213-249 (1970) and Keay, L. and Moser, P. W., "Differentiation of Alkaline Proteases from *Bacillus* Species" Biochemical and Biophysical Research Comm., Vol. 34, No. 5, pp. 600-604, (1969).

The subtilisin enzymes are broken down into two subclasses, subtilisin A and subtilisin B. In the subtilisin A grouping are enzymes derived from such species as *B. subtilis, B. liceniformis* and *B. pumilis*. Organisms in this sub-class produce little or not neutral protease or amylase.

In addition, other suitable enzymes are, for example, pancreatin, trypsin, collaginase, keratinase, carboxylase, aminopeptidase, elastase, and aspergillo-peptidas. A and B, pronase E (from *S. griseus*) and dispase (from *Bacillus polymyxa*), and thermolysin (from *Bacillus thermoproteolytics*).

An effective amount of the enzyme is to be used in the practice of this invention. Such amount will be that amount which effectively debrides necrotic tissue and liquefies pus in acute and chronic wounds. Such an amount will also be that amount which effects removal in a reasonable time (for example, over a 7 day period), of substantially all of such materials. The precise amount used for any particular use will depend on several factors, including the inherent activity of the enzyme, the number of applications intended for the wound, etc. In weight/volume terms, the enzyme preparations are seldom pure, and as earlier stated, it is expected that the enzyme source will be used in amounts of from 0.001% by weight to 20% by weight, preferably 0.01% to 10% by weight formulation. Precise amounts will vary with purity of the enzyme. As a basic yardstick, the working composition containing papain provides an activity between about 500 USP units/mg to 3000 USP units/mg, preferably 521.7 USP units/mg to 2700 USP units/mg.

A carrier for the topically active ingredient of the present invention can, in its broadest terms, be characterized as a surfactant emulsifier admixture having composition viscosity of from about 5000 cps to about 50,000 cps, preferably about 15,000 cps to about 40,000 cps as measured with a Brookfield viscometer.

Surfactant emulsifiers function to form relatively stable mixtures of oil and water. A surfactant is an organic compound consisting of two parts: One, a lipophilic portion, usually including a long hydrocarbon chain; and two, a hydrophilic portion which renders the compound sufficiently soluble or dispersible in water or another polar solvent. The combined hydrophobic and hydrophilic moieties enable the compound to be surface active, thus able to concentrate at the interface between a surfactant solution and another phase, such as a lipid phase. Surfactants are usually classified into: (1) Anionics, where the hydrophilic moiety of the molecule carries a negative charge; (2) cationics, where this moiety of the molecule carries a positive charge; and (3) nonionics, which have no charge, but commonly derive their hydrophilic moiety from polyhydroxy or polyethoxy structures. Other surfactants include amphoteric and zwitterionic surfactants.

Usable nonionic surfactants for this invention include pluronic polyols, sorbitan derivatives, ethoxylated alcohols, ethoxylated carboxylic acids, and fatty acid esters. Examples include sorbitan stearate, polysorbate, emulsifying wax (which is cetostearyl alcohol containing a polyoxyethylene derivative of a fatty acid ester of sorbitan), PEG-100 stearate, and glyceryl stearate. These are preferred emulsifiers.

The most preferred surfactant emulsifier is a complex reaction mixture of mono- and di-esters of ethoxylated and non-ethoxylated alcohols, and is Cryptoanionic meaning that the anionic phosphate groups are shielded by the alkyl chains.

These are blends of alkoxylated fatty alcohol mono- and diester phosphates with non-alkoxylated fatty alcohol mono- and diester phosphates. They produce oil-in-water emulsions and microemulsions possessing desirable emulsion stability. Therefore, in accordance with one embodiment of the present invention, there is provided an oil-in-water emulsifier composition of:

between about 10 percent and about 90 percent by weight of a blend of mono- and diester phosphates of alkoxylated fatty alcohols containing between about 12 and 22 carbon atoms and alkoxylated with between about 1 and about 50 moles of an alkylene oxide selected from the group consisting of ethylene oxide, propylene oxide and mixtures thereof, wherein the mono- and diester ratio is between about 10:90 and about 90:10; and between about 90 percent and about 10 percent by weight of a blend of mono- and diester phosphates of fatty alcohols containing between 12 and 22 carbon atoms, wherein the mono- and diester ratio is between about 10:90 and about 90:10; provided that the total amount of alkoxylation is within a range effective to provide both emulsion stability and oil deposition on keratin-containing substrates.

The emulsifier compositions of the present invention are preferably based on fatty alcohols containing between 14 and 20 carbon atoms, and more preferably are based on a blend of 16 and 18 carbon atom fatty alcohols. The emulsifier compositions of the present invention are preferably based on a ratio of alkoxylated fatty alcohol phosphate esters and non-alkoxylated fatty alcohol phosphate esters between about 20:80 and about 80:20, and more preferably between about 30:70 and about 70:30. The ratio of mono-esters to di-esters for both the alkoxylated and non-alkoxylated fatty alcohol phosphate esters is preferably between about 20:80 and 80:20 and more preferably between about 30:70 and about 70:30. Generally such surfactant emulsifiers are described in U.S. Pat. No. 6,117,915, the disclosure of which is incorporated by reference. Representative of these which are available from Croda, Inc. of Parsippa, N.J. is CRODAFOS CS-20 ACID. The INCI name of this material is Cetearyl Alcohol (and) Ceteth-20 Phosphate (and) Dicetyl Phosphate. The amount of the surfactant emulsifier will typically be from 1% to 20% of the composition generally 2% to 10%.

Other ingredients which can be employed include enzyme activators or cofactors such as urea, emollients, humectants, and preservatives. A combination of urea and papain for enzymatic activation is disclosed in U.S. Pat. No. 2,917,433 and therefore need not be generally disclosed herein in detail. Basically, the urea where used functions as a special cofactor of the papain ingredient, exerting its activating effect only when both ingredients 0.6 are in contact with digestible protein matter present in wounds. Papain is generally present in an amount from about 0.5 to 25% by weight of the total composition, and preferably 1 to 15% by weight. Urea is generally in an amount of from 5 to 25% by weight of the total composition, and preferably 5 to 15% by weight. In treating wounds which require debridement, some of the end products of proteolysis are muco-protein materials, which often produce an irritating action and other deleterious actions on the tissue in contact with said end products. In order to control such undesirable effects, it has been found desirable to incorporate in the compositions of the present invention a small amount of a water-soluble chlorophyll, generally in an amount in a range of 0.05 to 1% by weight of the total composition, and preferably in an amount of 0.1% to 0.5%. The water-soluble chlorophyll does not interfere with the desired proteolytic action.

Wound healing agents in addition are employed. They can be at levels of from 0.01% to 50% by weight of the composition. Suitable wound healing agents are of course well known and need not be described in detail herein. One example here used is chlorophyllin copper complex sodium.

Other ingredients which may be used include emollients at from about 1% to 10% by weight, humectants at about 1% to 10% by weight, and preservatives at generally less than 0.5% by weight but broadly in an amount of from 0.001% to 0.5% by weight.

The emollient portion serves to moisturize tissues at the wound site. This portion preferably has a weight up to about 25% of the total weight. More preferably, the emollient is mineral oil or petrolatum but can be a fatty alcohol in a level ranging from 1% to 15% by weight. Useful fatty alcohols include cetyl, stearyl, and behenyl alcohols. Fatty alcohols are particularly preferred because they function as surfactants, in addition to their emollient functions. Other oil emollients include lanolin or lanolin oil, octyl palmitate, and isopropyl myristate as well as other esters.

The humectant portion serves to stabilize the moisture content of the wound site. This portion preferably has a weight up to about 25% of the total cleanser weight. More preferably, the humectant portion is glycerine, propylene glycol, or butylene glycol at a level ranging from 1% to 15% by weight. The most preferred humectant is glycerine ranging from 2% to 10% by weight.

Overall, the pH of this system will generally be within the range of from 3 to 8 and preferably is controlled at a level at which the enzyme is most active. For a wound debrider, this is generally within the range of 4 to 7.

Pharmaceutical compositions as above described, can be effectively used with air hand pump systems using no aerosol, or if desired, they can be used in an aerosol pump system using an aerosol propellant. The product can be sprayed or dispensed as a foam. The formulation is always, providing these limits are met, viscous enough to not drip when applied to a vertical surface but is flowable to allow for pumping through the dispenser and uniformly provides the enzymatic wound debrider. Depending on the formulators choice, the product can be a hydrophilic ointment base or a hydrocarbon-based ointment. Examples 1 through 4 below show hydrophilic ointment wound debriders in a non-aerosol pump spray container. All the examples are offered to illustrate but not limit the inventor.

EXAMPLE 1

| INGREDIENTS | % w/w |
|---|---|
| Water | 58.21 |
| Urea | 10.0 |
| Chlorophyllin Copper Complex Sodium | 0.5 |
| Glycerin | 5.0 |
| Methylparaben | 0.20 |
| Mineral oil | 8.0 |
| Cetearyl Alcohol (and) Ceteth-20 Phosphate (and) Dicetyl Phosphate | 5.0 |
| Lactose, Anhydrous | 7.0 |
| Propylparaben | 0.05 |
| Papain | 6.04 |
| Sodium Hydroxide | q.s. pH |

EXAMPLE 2

| INGREDIENTS | % w/w |
|---|---|
| Water | 57.21 |
| Urea | 10.0 |
| Chlorophyllin Copper Complex Sodium | 0.5 |
| Glycerin | 5.0 |
| Methylparaben | 0.20 |
| Mineral Oil | 8.0 |
| Cetearyl Alcohol (and) Ceteth-20 Phosphate (and) Dicetyl Phosphate | 5.0 |
| Lactose, Anhydrous | 7.0 |
| Propylparaben | 0.05 |
| Papain | 6.04 |
| Potassium Phosphate | 1.00 |
| Sodium Hydroxide | q.s. pH |

EXAMPLE 3

| INGREDIENTS | % w/w |
|---|---|
| Water | 56.54 |
| Urea | 10.0 |
| Glycerin | 5.0 |
| Methylparaben | 0.2 |
| Mineral Oil | 8.0 |
| Cetearyl Alcohol (and) Ceteth-20 Phosphate (and) Dicetyl Phosphate | 5.0 |
| Lactose, Anhydrous | 12.91 |
| Propylparaben | 0.05 |
| Papain | 2.3 |
| Sodium Hydroxide | q.s. pH |

EXAMPLE 4

| INGREDIENTS | % w/w |
|---|---|
| Water | 55.54 |
| Urea | 10.0 |
| Glycerin | 5.0 |
| Methylparaben | 0.2 |
| Mineral Oil | 8.0 |
| Cetearyl Alcohol (and) Ceteth-20 Phosphate (and) Dicetyl Phosphate | 5.0 |
| Lactose, Anhydrous | 12.91 |
| Propylparaben | 0.05 |
| Papain | 2.3 |
| Potassium Phosphate | 1.0 |
| Sodium Hydroxide | q.s. pH |

Examples 1 through 4 illustrate products that have demonstrated efficacy in that the desired physical characteristics are achieved, they are pumpable, directionally sprayable and do not drip from wounds, even in a vertical position.

Example 5 through 8 are examples of hydrophilic ointment wound debriders in a pressurized aerosol foam container.

EXAMPLE 5

| INGREDIENTS | % w/w |
| --- | --- |
| Water | 65.21 |
| Urea | 10.0 |
| Chlorophyllin Copper Complex Sodium | 0.5 |
| Glycerin | 5.0 |
| Methylparaben | 0.20 |
| Mineral Oil | 1.0 |
| Cetearyl Alcohol (and) Ceteth-20 Phosphate (and) Dicetyl Phosphate | 4.0 |
| Lactose, Anhydrous | 7.0 |
| Propylparaben | 0.05 |
| Papain | 6.04 |
| Potassium Phosphate | 1.0 |
| Sodium Hydroxide | q.s. pH |
| Propellant AP-70 | q.s. |

EXAMPLE 6

| INGREDIENTS | % w/w |
| --- | --- |
| Water | 65.21 |
| Urea | 10.0 |
| Chlorophyllin Copper Complex Sodium | 0.5 |
| Glycerin | 5.0 |
| Methylparaben | 0.20 |
| Mineral Oil | 1.0 |
| Cetearyl Alcohol (and) Ceteth-20 Phosphate (and) Dicetyl Phosphate | 4.0 |
| Lactose, Anhydrous | 7.0 |
| Propylparaben | 0.05 |
| Papain | 6.04 |
| Potassium Phosphate | 1.0 |
| Sodium Hydroxide | q.s. pH |
| Propellant Dymel 134a/P | q.s. |

EXAMPLE 7

| INGREDIENTS | % w/w |
| --- | --- |
| Water | 63.54 |
| Urea | 10.0 |
| Glycerin | 5.0 |
| Methylparaben | 0.2 |
| Mineral Oil | 1.0 |
| Cetearyl Alcohol (and) Ceteth-20 Phosphate (and) Dicetyl Phosphate | 4.0 |
| Lactose, Anhydrous | 12.91 |
| Propylparaben | 0.05 |
| Papain | 2.3 |
| Potassium Phosphate | 1.0 |
| Sodium Hydroxide | q.s. pH |
| Propellant AP-70 | q.s. |

EXAMPLE 8

| INGREDIENTS | % w/w |
| --- | --- |
| Water | 63.54 |
| Urea | 10.0 |
| Glycerin | 5.0 |
| Methylparaben | 0.2 |
| Mineral Oil | 1.0 |
| Cetearyl Alcohol (and) Ceteth-20 Phosphate (and) Dicetyl Phosphate | 4.0 |
| Lactose, Anhydrous | 12.91 |
| Propylparaben | 0.05 |
| Papain | 2.3 |
| Potassium Phosphate | 1.0 |
| Sodium Hydroxide | q.s. pH |
| Propellant Dymel 134a/P | q.s. |

The aerosol compositions of examples 5-8 also perform satisfactorily as a directionally oriented spray foam, do not drip in normal use, and will not run out of a wound after normal application.

Various non-aerosol pump sprayers and aerosol foam actuators can be utilized to give the desired spray or foam. Examples are Calmar Mark IV, Calmar Mark VI, Calmar Mark VII, Precision Valve "City" Foam Spout, Precision Valve Power Jet, and Precision Valve Kosmos Ext/Nozzle.

From the above examples 1-8, it can be seen that the invention successfully accomplishes it's primary objective, as well as others.

What is claimed is:

1. A spray-on topical wound debrider composition comprising:
    (a) an effective amount of a proteolytic enzyme wound debrider; and
    (b) a surfactant emulsifier admixture to provide an emulsion containing the wound debrider and having a composition viscosity of from about 5000 cps to about 50,000 cps, wherein the surfactant emulsifier is present in an amount of from 1% by weight to 20% by weight of the total composition and wherein the surfactant emulsifier is a cryptoanionic comprising an alkoxylated fatty alcohol and mono and diester phosphates; and
    (c) at least one wound healing agent, emollient, humectant, preservative, or anti-microbial,
    wherein the composition is capable of forming a mist, spray or foam which will not drip significantly after application.

2. The composition of claim 1 wherein the composition is contained in a non-aerosol pump container.

3. The composition of claim 1 wherein the composition is contained in a pressurized aerosol container.

4. The composition of claim 1 wherein the proteolytic enzyme is present at an amount of from 0.001% to 20% by weight of the composition.

5. The composition of claim 4 wherein the proteolytic enzyme is present at an amount of from 0.01% to 10% by weight of the composition.

6. The composition of claim 1 wherein the surfactant emulsifier admixture provides a composition viscosity of from about 15,000 cps to about 40,000 cps.

7. The composition of claim 1 which has a pH of from about 3 to about 8.

8. The composition of claim 7 which has a pH of from about 4 to about 7.

9. The composition of claim 1 wherein the proteolytic enzyme is selected from the group consisting of papain, trypsin, chymo-trypsin, streptokinaise, streptodormase, ficin, pepsin, bromelin, thermolysin, thermoase, and subtilisin.

10. The composition of claim 9 where in the proteolytic enzyme is selected from the group consisting of papain, trypsin, and thermolysin, and thermoase.

11. The composition of claim 1, wherein the surfactant emulsifier is present in an amount from 2% by weight to 10% by weight of the total composition.

12. A spray-on topical wound debrider composition comprising:
(a) an effective amount of a proteolytic enzyme wound debrider; and
(b) a surfactant emulsifier admixture to provide an emulsion containing the wound debrider and having a composition viscosity of from about 5000 cps to about 50,000 cps; and
(c) at least one wound healing agent, emollient, humectant, preservative, or anti-microbial,
wherein the composition is contained in a pressurized aerosol container and is capable of forming a mist, spray or foam which will not drip significantly after application.

13. The composition of claim 12 wherein the proteolytic enzyme is present at an amount of from 0.001% to 20% by weight of the composition.

14. The composition of claim 13 wherein the proteolytic enzyme is present at an amount of from 0.01% to 10% by weight of the composition.

15. The composition of claim 12 wherein the surfactant emulsifier admixture provides a composition viscosity of from about 15,000 cps to about 40,000 cps.

16. The composition of claim 12 which has a pH of from about 3 to about 8.

17. The composition of claim 16 which has a pH of from about 4 to about 7.

18. The composition of claim 12 wherein the proteolytic enzyme is selected from the group consisting of papain, trypsin, chymo-trypsin, streptokinaise, streptodormase, ficin, pepsin, bromelin, thermolysin, thermoase, and subtilisin.

19. The composition of claim 18 where in the proteolytic enzyme is selected from the group consisting of papain, trypsin, and thermolysin, and thermoase.

20. The composition of claim 12 wherein the surfactant emulsifier is present in an amount of from 1% to 20% by weight of the total composition.

21. The composition of claim 12 wherein the surfactant emulsifier is present in an amount of from 2% by weight to 10% by weight of the total composition.

22. The composition of claim 12 wherein the surfactant emulsifier is selected from the group consisting of anionics, cationics, nonionics, and cryptoanionics.

23. The composition of claim 22, wherein the surfactant emulsifier is a cryptoanionic.

24. The composition of claim 23, wherein the cryptoanionic comprises an alkoxylated fatty alcohol and mono and diester phosphates.

25. A spray-on topical wound debrider composition comprising:
(a) an effective amount of a proteolytic enzyme wound debrider; and
(b) a surfactant emulsifier admixture to provide an emulsion containing the wound debrider and having a composition viscosity of from about 5000 cps to about 50,000 cps, wherein the surfactant emulsifier is present in an amount of from 1% by weight to 20% by weight of the total composition and wherein the surfactant emulsifier is a cryptoanionic comprising an alkoxylated fatty alcohol and mono and diester phosphates; and
wherein the compositions is contained in a pressurized aerosol container and is capable of forming a mist, spray or foam which will not drip significantly after application.

26. The composition of claim 25 wherein the proteolytic enzyme is present at an amount of from 0.001% to 20% by weight of the composition.

27. The composition of claim 26 wherein the proteolytic enzyme is present at an amount of from 0.01% to 10% by weight of the composition.

28. The composition of claim 25 wherein the surfactant emulsifier admixture provides a composition viscosity of from about 15,000 cps to about 40,000 cps.

29. The composition of claim 25, further comprising at least one wound healing agent, emollient, humectant, preservative, or anti-microbial.

30. The composition of claim 25 which has a pH of from about 3 to about 8.

31. The composition of claim 30 which has a pH of from about 4 to about 7.

32. The composition of claim 25 wherein the proteolytic enzyme is selected from the group consisting of papain, trypsin, chymo-trypsin, streptokinaise, streptodormase, ficin, pepsin, bromelin, thermolysin, thermoase, and subtilisin.

33. The composition of claim 32 where in the proteolytic enzyme is selected from the group consisting of papain, trypsin, and thermolysin, and thermoase.

34. The composition of claim 25 wherein the surfactant emulsifier is present in an amount of from 2% by weight to 10% by weight of the total composition.

* * * * *